(12) United States Patent
Cohen et al.

(10) Patent No.: US 7,477,378 B2
(45) Date of Patent: Jan. 13, 2009

(54) METHOD FOR CORRELATING SPECTROSCOPIC MEASUREMENTS WITH DIGITAL IMAGES OF CONTRAST ENHANCED TISSUE

(75) Inventors: Jeffrey Cohen, Pittsburgh, PA (US); John S. Maier, Pittsburgh, PA (US)

(73) Assignee: ChemImage Corporation, Pittsburgh, PA (US)

( * ) Notice: Subject to any disclaimer, the term of this patent is extended or adjusted under 35 U.S.C. 154(b) by 198 days.

(21) Appl. No.: 11/527,839

(22) Filed: Sep. 27, 2006

(65) Prior Publication Data

US 2007/0070343 A1    Mar. 29, 2007

Related U.S. Application Data

(60) Provisional application No. 60/720,709, filed on Sep. 27, 2005.

(51) Int. Cl.
*G01N 3/44* (2006.01)
(52) U.S. Cl. ........................... 356/301; 356/326
(58) Field of Classification Search ........... 356/326, 356/73, 301, 317–318; 702/189
See application file for complete search history.

(56) References Cited

U.S. PATENT DOCUMENTS

| | | | |
|---|---|---|---|
| 4,513,438 A | 4/1985 | Graham et al. | |
| 6,241,662 B1 | 6/2001 | Richards-Kortum et al. | |
| 6,690,464 B1 * | 2/2004 | Lewis et al. | 356/326 |
| 2006/0050278 A1 * | 3/2006 | Treado et al. | 356/417 |
| 2006/0155195 A1 * | 7/2006 | Maier et al. | 600/476 |
| 2007/0070343 A1 * | 3/2007 | Cohen et al. | 356/301 |
| 2007/0127022 A1 * | 6/2007 | Cohen et al. | 356/326 |
| 2007/0244395 A1 * | 10/2007 | Wang et al. | 600/476 |

FOREIGN PATENT DOCUMENTS

WO    2006037892    7/2008

* cited by examiner

*Primary Examiner*—Kara E Geisel
(74) *Attorney, Agent, or Firm*—Morgan Lewis & Bockius LLP (57) ABSTRACT

A system and method of correlating Raman measurements with digital images of a sample so to classify the sample's disease state. A spectroscopic data set is obtained for the sample positioned in the field of view of a spectroscopic device. With the sample removed from the field of view, the sample is treated with a contrast enhancing agent. The treated sample is repositioned in the spectroscopic device's field of view and a digital image of the treated sample is obtained. The spectroscopic data set is linked with the digital image by defining a transformation to map the image spatial coordinates of the digital image to the spectral spatial coordinates of the spectroscopic data. For the spectroscopic data set of the sample, a database is searched to identify a spectroscopic data set, of a known sample having well characterized pathology, which matches the sample's spectroscopic data set.

26 Claims, 10 Drawing Sheets

METHOD FOR CORRELATING SPECTROSCOPIC MEASUREMENTS WITH DIGITAL IMAGES OF CONTRAST ENHANCED TISSUE

RELATED APPLICATIONS

This application claims the benefit of U.S. Provisional Application No. 60/720,709, filed Sep. 27, 2005 entitled "Method for Correlating Raman Measurements with Digital Images of Stained Tissue" which is incorporated herein by reference in its entirety.

FIELD OF DISCLOSURE

The present invention relates generally to a method and system to use spectroscopic measurements to classify a disease state through a correlation of spectroscopic measurements and digital images.

BACKGROUND

Spectroscopy and imaging has held promise for adding quantitative and objective analysis of tissue samples. However, the application of spectroscopic measurements to tissue analysis is limited by the inability to correlate the spectroscopic data with histopathology which is evident in image data. This results from the interference of traditional contrasting agents with spectroscopic measurements. The present disclosure describes an approach to overcome this limitation.

SUMMARY

The present disclosure provides for a method of correlating spectroscopic measurements with digital images of treated tissue and using the correlation to classify a disease state of a sample. A sample is positioned in a field of view of a spectroscopic device. A spectroscopic data set is obtained for the sample positioned in the field of view. The positional information about the field of view is stored. After the sample is treated with a contrast enhancing agent, the treated sample is repositioned in the field of view of the spectroscopic device using the stored positional information about the field of view. A digital image of the treated sample positioned in the field of view is obtained. The sample's spectroscopic data set is linked with the digital image by defining a transformation to map the image spatial coordinates of the digital image to the corresponding spectral spatial coordinates of the spectroscopic data.

In one embodiment, the spectroscopic data set includes a plurality of Raman spectra and a plurality of spatially accurate wavelength resolved Raman images.

In another embodiment, a database having a plurality of spectroscopic data sets is provided. Each spectroscopic data set is linked to a corresponding digital image, and each spectroscopic data set is associated with a known sample having well characterized pathology. Each corresponding digital image is associated with the known sample treated with a contrast enhancing agent. For the spectroscopic data set of the sample, the database is searched to identify a spectroscopic data set of a known sample matching the sample's spectroscopic data set.

The present disclosure further provides for a storage medium containing machine readable program code, which, when executed by a processor, causes the processor to perform a series of steps. A first spectroscopic data set is obtained for a sample positioned in a field of view of a spectroscopic device. The positional information about the field of view is stored. After the sample is treated with a contrast enhancing agent, the repositioning of the treated sample in the field of view of the spectroscopic device is monitored using the stored positional information for the field of view. A digital image of the treated sample positioned in the field of view is obtained. The digital image and the first spectroscopic data set are stored. For the first spectroscopic data set, a database having a plurality of spectroscopic data sets is searched to identify a second spectroscopic data set matching the first spectroscopic data set.

The present disclosure further provides for a system including a spectroscopic device, an imaging device, a machine readable program code containing executable program instructions; and a processor operatively coupled to the spectroscopic device and the imaging device and configured to execute the machine readable program code so as to perform a series of steps.

In one embodiment, the system further includes a database having a plurality of spectroscopic data sets and a plurality of digital images of known samples having well characterized pathology.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

In the drawings.

DETAILED DESCRIPTION OF THE DISCLOSURE

Reference will now be made in detail to the preferred embodiments of the present invention, examples of which are illustrated in the accompanying drawings. Wherever possible, the same reference numbers will be used throughout the drawings to refer to the same or like parts.

The present disclosure provides for a method to correlate spectroscopic measurements of samples with the spatial locations on digital images of contrast enhanced tissue. The correlation allows a user to classify the disease state of an unknown sample. Because treating a sample with a contrast enhancing agent typically interferes with spectroscopic measurements, spectroscopic data, for the unknown sample, are obtained prior to treating the unknown with the agent. The field of view of the spectroscopic measurement is stored so that the sample may be repositioned in the same field of view for later digital image measurements. The sample is then treated with the contrast enhancing agent and the unknown sample repositioned in the previously stored field of view. An image of the contrast enhanced sample is then obtained. The image of the contrast enhanced sample is linked to the spectroscopic measurement through a procedure of defining a mathematical translation of the relative spatial coordinates of the image of the contrast enhanced sample to the corresponding spatial coordinates of the spectroscopic measurements. The spatial coordinates of the digital image and the spatial coordinates of the spectroscopic measurements may be stored in a database. Because the two independent measurements are made on the same field of view, relative positions within the two datasets will correspond to the same location on the sample. By way of example, a single point halfway between the top and bottom and halfway between the left and right of the boundaries of the digital image of the contrast enhanced sample (at the center of the digital image) corresponds to the spectral measurement halfway between the top and bottom and halfway between the left and right of the boundaries of the set of spectroscopic measurements. By way of second example, the upper right quadrant of the digital image of the contrast enhanced sample corresponds to the upper right quadrant of a wavelength resolved spectra image obtained in set of spectroscopic measurements. This mathematical translation is in relative coordinates thus, there is no requirement that both images have the same pixel size or shape.

Through this procedure, the spectroscopic measurements are effectively linked to the digital images of the contrast enhanced sample. The method allows a user to classify the disease state of an unknown sample, based on its spectroscopic data, by searching a database containing spectroscopic information for known samples with well characterized pathology. This search can be performed on selected regions of the spectral data set. The method enables the search to be focused on selected regions of the spectral data set, containing spatially accurate wavelength resolved images, where the selected regions are targeted through use of the digital image of the contrast enhanced sample which is linked to the spectral data as described above. By way of example, in a case where a field of view contains both epithelial tissue and stromal tissue, a more accurate search of the database of spectral information can be obtained by selecting a subset spectral data corresponding to the epithelial tissue to be searched against the database. This subset of the spectral data can be determined after the digital image of the contrast enhanced sample is linked to the spectral measurements. The subset of spectral data is determined by identifying the spatial coordinates for a region of interest on the digital image of the contrast enhanced sample (corresponding to the epithelium for example), making the mathematical translation to identify the corresponding region of interest in the spectral dataset. The database is searched for the spectral data corresponding to the subset of the spectral data defined by the mapping of the region of interest from the digital image of the contrast enhanced sample to the spectral data set. This subset is searched against the database for matches for the spectral character of the sample.

A digital image of the sample prior to treatment with a contrast enhancing agent may also be obtained and stored. The digital image may be used if subtle positional differences are present between the images of the treated and untreated samples. In this embodiment, the digital image of the untreated sample provides the positioning of the regions of interest to resolve any discrepancy.

As described above, the image linking scheme is a tool for selecting which subset of the spectral image data for the selected region of interest is used for disease classification through searching the database. This is described above for a manual approach to select a region of interest on the digital image which is linked to the spectral image. Automated approaches based on image segmenting could equally be applied to select a region of interest using a digital image associated with a spectral image. For instance an automated algorithm for determining which regions of a digital image correspond to the nuclei of cells could be used to select the subset of the spectral image which is compared to the database. Moreover, there is no restriction that a subset of the spectral dataset is contiguous spatially.

Figure 1:
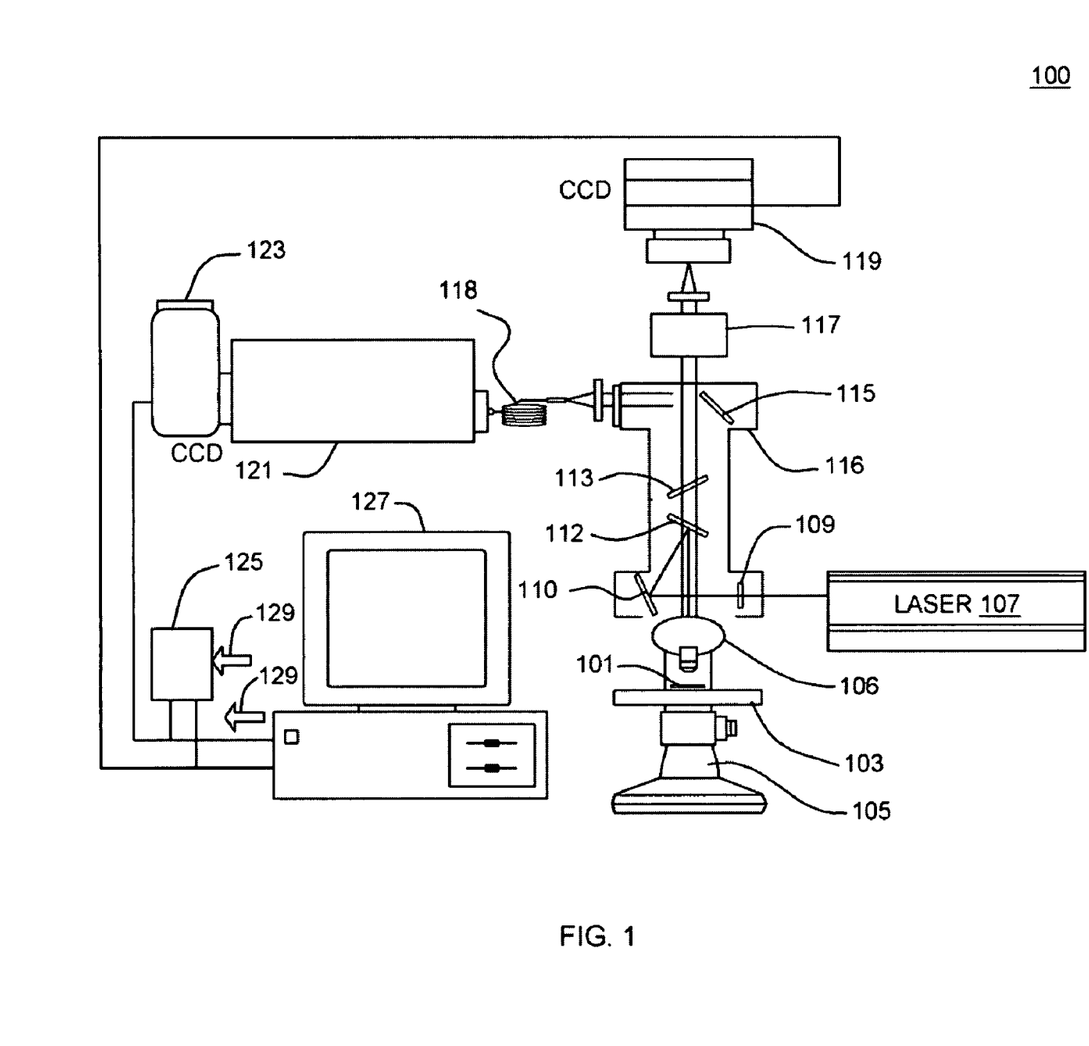
FIG. 1 schematically represents an exemplary system of the present disclosure.

FIG. 1 schematically represents an exemplary system 100 used to perform the methods of the present disclosure. System 100 includes, in a single platform, an imaging device in the form of a microscope objective 106, a spectroscopic device in the form of an imaging spectrometer 117 or a dispersive spectrometer 121, a processor 127, a database 125 and a microscope stage 103. System 100 further includes laser light source 107, white light source 105, bandpass filter 109 to remove $SiO_2$ bands arising from a laser excitation fiber optic. The laser light is directed to a band reject optical filter 110 and propagated through an imaging objective 106 to illuminate the sample 101. Objective 106 collects photons emanating from the sample 101. Notch filters 112 and 113 reject light at the laser wavelength.

Though the discussion herein focuses on the system illustrated in FIG. 1, the practice of the method of this disclosure is not limited to such a system. An alternative system with the ability to deliver digital images and spectroscopic data sets is described in U.S. Pat. No. 7,046,359 entitled "System and Method for Dynamic Chemical Imaging" which is incorporated herein by reference in its entirety.

Figure 2A:
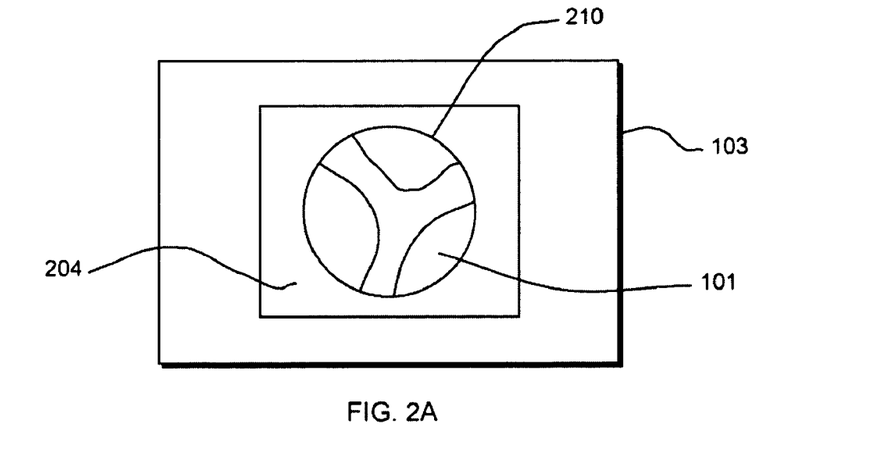
FIGS. 2A-2C illustrate the operation of an exemplary device used in the system of the present disclosure.
Figure 2B:
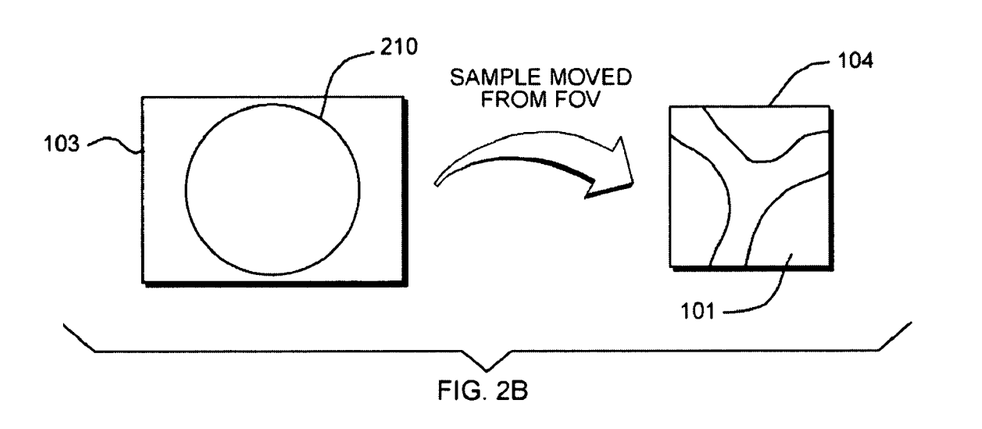
Figure 2C:
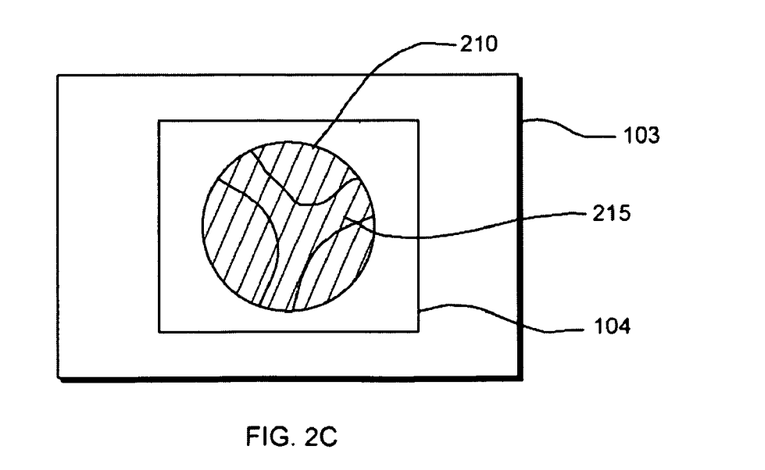

Sample 101 is an unknown sample for which a user would like to classify its disease state. Sample 101 may include a variety of samples such as tissue, tissue microarray, protein microarray, DNA microarray, and western blot. In one embodiment, sample 101 includes tissue. In another embodiment, the tissue includes kidney tissue, prostate tissue, lung tissue, colon tissue, bone marrow tissue, brain tissue, red blood tissue, breast tissue and cardiac muscle tissue FIGS. 2A-2C illustrate sample 101 supported on a substrate 204 which is positioned on an exemplary XYZ translational microscope stage 103. Microscope stage 103 includes a movable stage such as an automated XYZ translational microscope stage 103 which functions to position the sample 101 in field of view 210 of the collection optics of spectroscopic devices 117 or 121. Sample 101 is positioned in the field of view 210 of spectroscopic device 117, FIG. 2A. Imaging device 106 and spectroscopic devices 117 and 121 are aligned to have the same field of view 210. The positional information for the field of view 210 is stored for later reference. In one embodiment, the positional information is the center of the field of view relative to some origin fixed on the sample holder. Spectroscopic devices 117 and 121 are used to obtain a spectroscopic data set for sample 101 positioned in the field of view 210. In one embodiment, spectroscopic devices 117 or 121 are used to obtain Raman data sets for a tissue sample and imaging device 106 is used to obtain digital images of the tissue sample. In another embodiment, spectroscopic devices 117 or 121 are used to obtain fluorescence datasets for a sample and imaging device 106 is used to obtain digital images of the tissue sample. Sample 101 is then moved from the field of view 210 using the XYZ translational microscope stage, as shown in FIG. 2B. While sample 101 is positioned outside the field of view 210, sample 101 is treated with a contrast enhancing agent. The contrast enhancing agent includes a stain, a haematoxylin and eosin stain, phosphotungstic acid haematoxylin, silver nitrate, silver metal, gold ions, gold metal, osmium (VIII) oxide and immunohistochemically targeted fluorescent stains. In one embodiment, the contrast enhancing agent includes a haematoxylin or eosin stain. The treated sample 215 is repositioned within the field of view 210 of spectroscopic devices 117 and 121 using the stored positional information, FIG. 2C. The imaging device 106 is used to obtain a digital image of the treated sample 215. In one embodiment, imaging device 106 is used to obtain a digital image of a tissue sample treated with a haematoxylin stain. By these steps, a user is able to obtain spectroscopic data of a sample before treatment with the contrast enhancing agent and digital images of the sample after treatment with the contrast enhancing agent. The spectroscopic data is obtained from the same spatial locations as observed in the digital images by storing the positional information of the field of view of spectroscopic devices 117 and 121.

To obtain a digital image, sample 101 is illuminated using a broad band light source 105, as illustrated in FIG. 1. In one embodiment, the white light source 105 is located under the sample 100 where system 100 operates a transmittance image mode. In a second embodiment, the white light source 105 is located above the sample 101 when system 100 operates in reflectance image mode. The transmitted or reflected light from the sample 101, positioned on the XYZ translational microscope stage 103, is collected using microscope objective 106. In one embodiment, microscope objective 106 includes an infinity-corrected microscope objective. The resulting digital image is detected by a CCD detector (not shown) and stored in database 125.

Sample 101 is also illuminated with a laser light source 107. Light source 107 can include any conventional photon source, including laser, LED, and other IR or near IR devices. Light source 107 may also be selected to provide evanescence illumination of the sample. In one embodiment, the line width of the laser light source 107 is in the range of about 15-25 $cm^{-1}$. In another embodiment, laser epi-illumination is provided by light source 107, such as a Spectra Physics Millenia II Nd:YVO$_4$ laser beamed directly into the microscope optic. The monochromatic light reaching sample 101 illuminates the sample and photons are either scattered or emitted from different locations on or within the sample. The term emitted includes a wide range of optical processes including fluorescence, phosphorescence, photoluminescence, electroluminescence, chemiluminescence, sonoluminescence, thermoluminescence and even upconversion. Emitted photons or Raman scattered photons are collected by microscope objective 106 and directed to spectrometer 121 or imaging spectrometer 117.

Spectrometer 121 and imaging spectrometer 117 function to produce spectroscopic data sets of sample 101. A spectroscopic data set includes one or more of the following: a plurality of spectra and a plurality of spatially accurate wavelength resolved spectroscopic images. In one embodiment, the plurality of spectra includes a plurality of Raman spectra and the plurality of spatially accurate wavelength resolved spectroscopic images include a plurality of spatially accurate wavelength resolved Raman images. In another embodiment, the plurality of spectra includes a plurality of fluorescence spectra and the plurality of spatially accurate wavelength resolved spectroscopic images include a plurality of spatially accurate wavelength resolved fluorescence images. In yet another embodiment, the plurality of spectra includes a plurality of transmittance spectra and the plurality of spatially accurate wavelength resolved spectroscopic images include a plurality of spatially accurate wavelength resolved transmittance images. The spectroscopic data set may contain spectroscopic subsets where the subset includes a plurality of spectra for the region of interest selected from the digital image The plurality of spectra are obtained using dispersive spectrometer 121. A swing away mirror 115 is placed before filter 117 to redirect the emitted or Raman scattered photons to a fiber-optic 118. The other end of fiber-optic 118 is configured in a linear geometry and is focused on the entrance slit of a dispersive spectrometer 121. The plurality of spectra are detected by CCD detector 123 located at the exit focal plane of the spectrometer 121.

Referring still to FIG. 1, an imaging spectrometer 117 is used to generate the plurality of spatially accurate wavelength resolved spectroscopic images. The imaging spectrometer includes a two-dimensional tunable filter, such as electro-optical tunable filters, liquid crystal tunable filter ("LCTF") or acousto-optical tunable filter ("AOTF"). The electro-optical filter (interchangeably, tunable filters) sequentially passes the emitted or Raman scattered photons in each of a plurality of predetermined wavelength bands. The plurality of predetermined wavelength bands include specific wavelengths or ranges of wavelengths. In one embodiment, the predetermined wavelength bands include wavelengths characteristic of the sample undergoing analysis. The wavelengths that can be passed through tunable filter 140 may range from 200 nm (ultraviolet) to 2000 nm (i.e., the far infrared). The choice of tunable filter depends on the desired optical region and/or the nature of the sample being analyzed. The two-dimensional tunable filter includes a Fabry Perot angle tuned filter, an acousto-optic tunable filter, a liquid crystal tunable filter, a Lyot filter, an Evans split element liquid crystal tunable filter, a Solc liquid crystal tunable filter, a spectral diversity filter, a photonic crystal filter, a fixed wavelength Fabry Perot tunable filter, an air-tuned Fabry Perot tunable filter, a mechanically-tuned Fabry Perot tunable filter, a liquid crystal Fabry Perot tunable filter. The tunable filer is selected to operate in one or more of the following spectral ranges: the ultraviolet (UV), visible, near infrared, and mid-infrared.

The plurality of spectra are detected by detector 123 and the plurality of spatially accurate wavelength resolved spectroscopic images are detected by detector 119. Detector 119 detects, in a spatially accurate manner, the emitted, Raman scattered or transmitted photons passed by imaging spectrometer 117. Detectors 119 and 123 may include a digital device such as for example an image focal plane array ("FPA") or CCD or CMOS sensor. The optical region employed to characterize the sample of interest governs the choice of two-dimensional array detector. For example, a two-dimensional array of silicon charge-coupled device ("CCD") detection elements can be employed with visible wavelength emitted or Raman scatter photons, while gallium arsenide (GaAs) and gallium indium arsenide (GaInAs) FPA detectors can be employed for image analyses at near infrared wavelengths. The choice of such devices depends on the type of sample being analyzed.

The spectroscopic data set and the digital image of the sample 101 are stored in database 125, shown in FIG. 1. For sample 101, its spectroscopic data set is linked with the digital image of the sample 101. In one embodiment, Raman spectroscopic data for a sample is linked to a digital image of the sample treated with haematoxylin stain and or eosin. As was discussed above, the digital image and the spectroscopic data set are linked through a transformation. The digital image, of the treated sample, may be characterized by a plurality of spatial coordinates. These spatial coordinates describe the x and y positions of the various features observed in the digital image. The spatially accurate wavelength resolved images, that are part of the spectroscopic data sets, are also characterized by a plurality of spatial spectral coordinates. The digital image and the spectroscopic data set are then linked through a transformation that maps the plurality spatial coordinates of the digital image to the corresponding plurality of spatial coordinates of the spectroscopic data set for sample 101.

Database 125 also stores a plurality of spectroscopic data sets and digital images for known samples. The known samples have well characterized pathology of various disease conditions made through pathological examination of the digital images. The disease conditions include cancer, infection, stroke, ischemia, metabolic disorder, autoimmune disorders and heart attack. In database 125, each spectroscopic data set is associated with the known sample and linked to the corresponding digital image of the known sample where the sample has been treated with a contrast enhancing agent.

To determine the spectroscopic data set or subset of sample 101 for analysis, the spatial coordinates of a region of interest are identified from the digital image of the treated sample. A corresponding region of interest is then identified for the spectroscopic data set or subset based on the transformation discussed above. The spectroscopic data set or subset includes one or more spatially accurate wavelength resolved spectroscopic images.

Processor 127 is configured to execute a machine readable program code 129 to search the database 125. For the spectroscopic data set or subset of the sample 101 under analysis, the database is searched to identify a spectroscopic data set, for a known sample having well characterized pathology, matching the spectroscopic data set of the sample 101. In one embodiment, database 125, is searched for a Raman data set for a known sample that matches the Raman spectrum of a tissue sample from a subject which is suspected of having a disease. The database can be searched using a variety of similarity metrics. The metrics include Euclidean Distance, the Spectral Angle Mapper (SAM), the Spectral Information Divergence (SID), Mahalanobis distance metric and spectral unmixing. A spectral unmixing metric is disclosed in U.S. Pat. No. 7,072,770 B1 entitled "Method for Identifying Components of a Mixture via Spectral Analysis," which is incorporated herein by reference in its entirety.

The use of Raman spectroscopy to detect diseases is disclosed in the following: U.S. patent appilication Ser. No. 11/269,596 entitled "Cytological Methods for Detecting Disease Conditions Such as Malignancy by Raman Spectroscopic Imaging," filed Nov. 9, 2005; U.S. patent application Ser. No. 11/000,545, filed Nov. 20, 2004, entitled "Raman Molecular Imaging for Detection of Bladder Cancer, which are incorporated by reference herein it their entirety. In one embodiment, the database is searched to determine if the tissue sample is indicative of bladder cancer by the sample's Raman spectra data sets. Cancerous bladder cells exhibit significant Raman scattering at an RS value of about 1584 $cm^{-1}$, relative to non-cancerous bladder cells. The intensity of Raman scattering at this RS values increases with increasing grade of bladder cancer. Other RS values at which Raman scattering is associated with the cancerous state of bladder cells include about 1000, 1100, 1250, 1370, and 2900 $cm^{-1}$. Furthermore, there is a generalized increase in Raman scattering at RS values in the range from about 1000 to 1650 $cm^{-1}$ and in the range from about 2750 to 3200 $cm^{-1}$ in bladder cancer cells, relative to non-cancerous bladder cells, and this generalized increase is more pronounced in the range of RS values from about 1530 to 1650 $cm^{-1}$. These RS values and ranges are useful for assessing the cancerous state of bladder cells.

Figure 3:
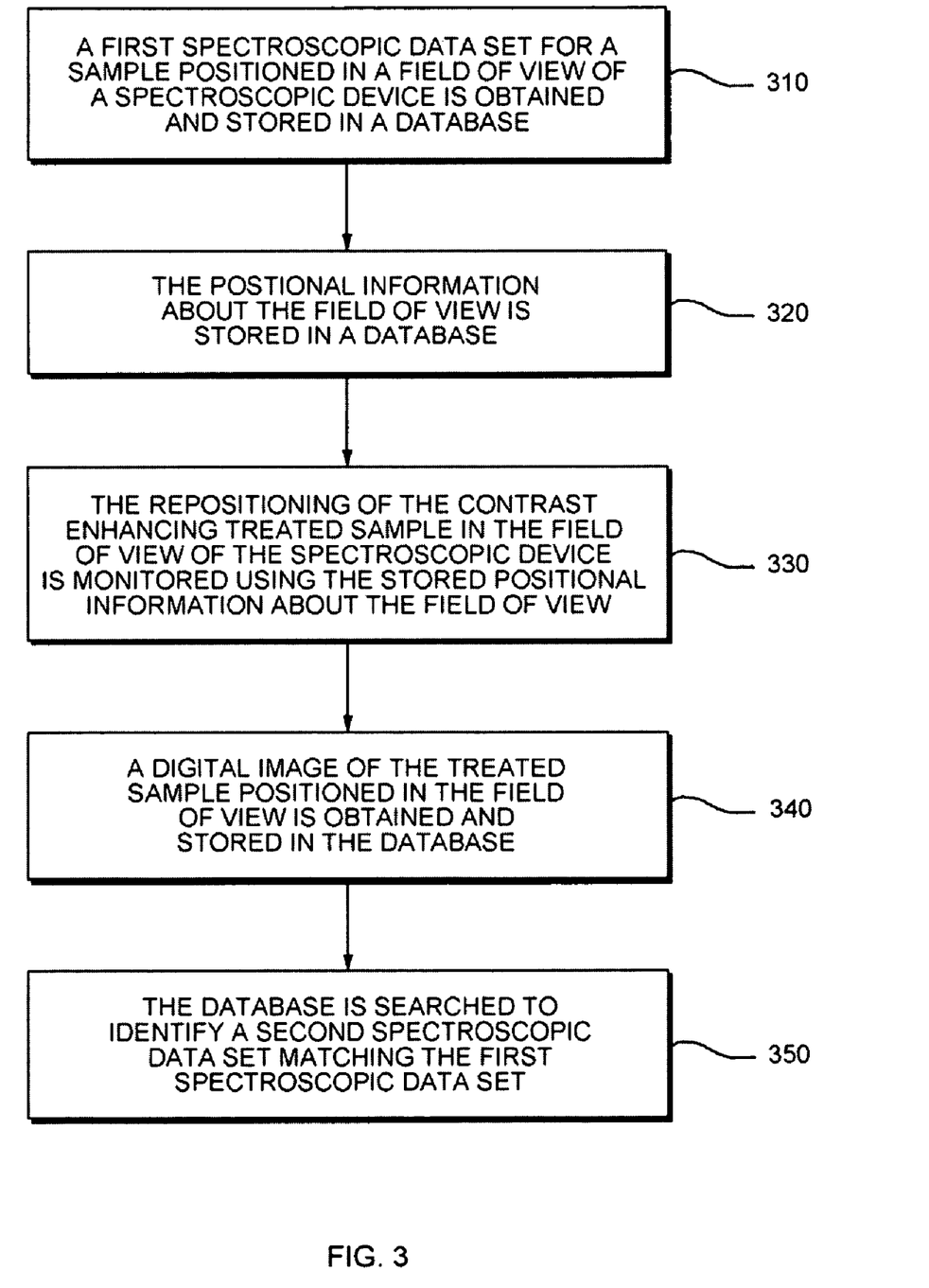
FIG. 3 is a flow chart illustrating an exemplary method of the present disclosure.

Processor 127 is also configured to execute machine readable program code containing executable program instructions to perform a variety of functions. These functions are illustrated in FIG. 3 which shows a flow chart for a method of the present disclosure. In step 310, a first spectroscopic data set for a sample positioned in a field of view of a spectroscopic device is obtained and stored in a database. In step 320, the positional information about the field of view is stored in a database. In step 330, the repositioning of the contrast enhancing treated sample in the field of view of the spectroscopic device is monitored using the stored positional information about the field of view. In step 340, a digital image of the treated sample positioned in the field of view is obtained and stored in the database. The field of view is the same field of view at that in step 310. In step 350, the database is searched to identify a second spectroscopic data set matching the first spectroscopic data set or a subset of the spectroscopic dataset chosen using the linked digital image as a guide. The second spectroscopic data set is for a known sample having well characterized pathology.

EXAMPLES

Figure 4:
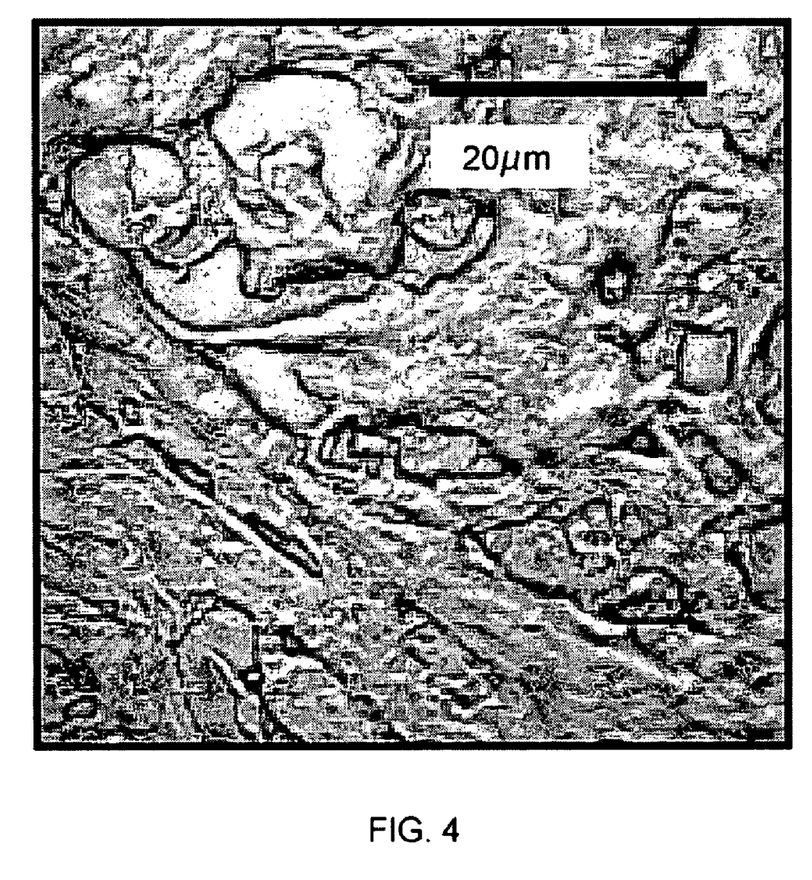
FIG. 4 shows a digital image of kidney tissue before treatment with a contrast enhancing agent obtained by an embodiment of the present disclosure.
Figure 5A:
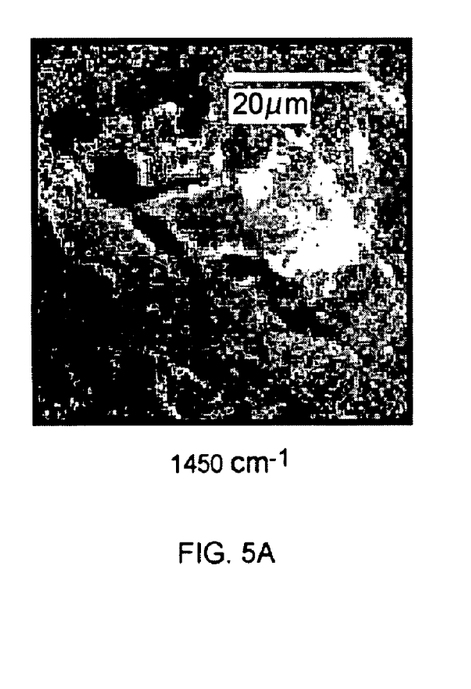
FIGS. 5A-5C show spatially accurate wavelength resolved Raman images of kidney tissue.
Figure 5B:
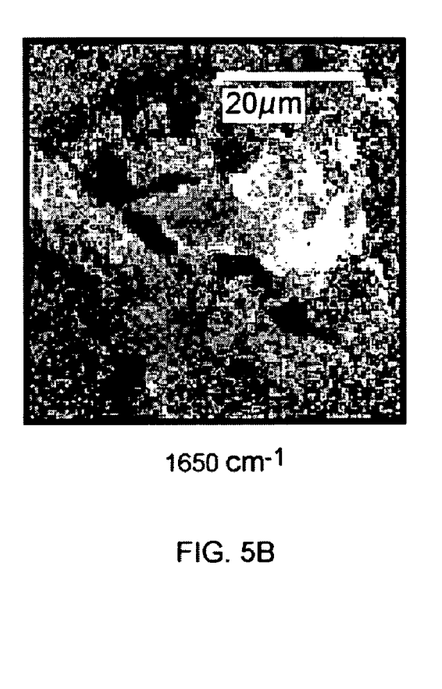
Figure 5C:
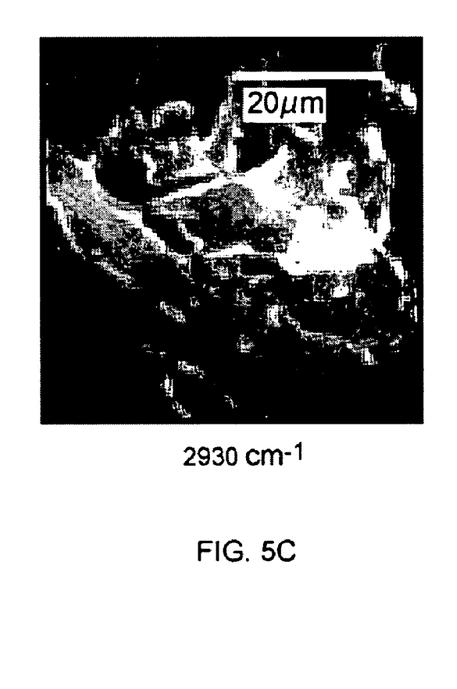
Figure 6A:
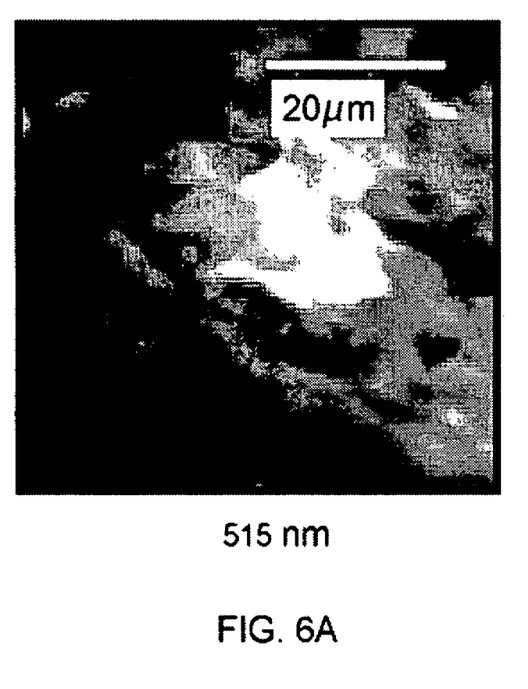
FIGS. 6A-6B show spatially accurate wavelength resolved fluorescence images of kidney tissue.
Figure 6B:
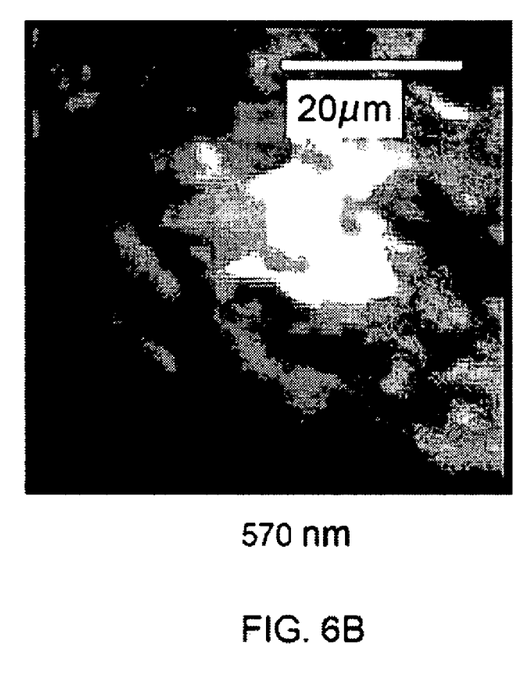
Figure 7:
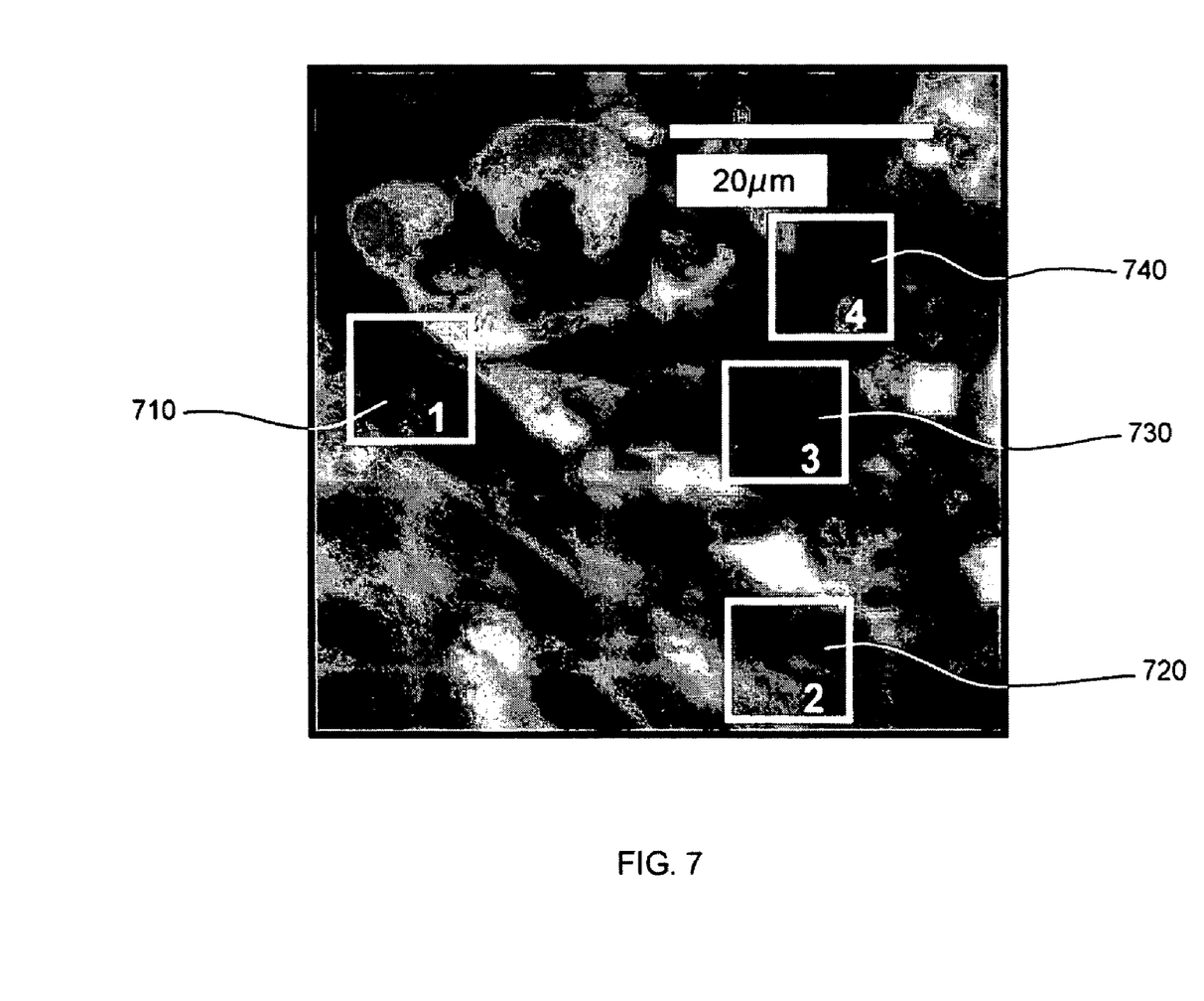
FIG. 7 shows a digital image of kidney tissue after treatment with a contrast enhancing agent.
Figure 8:
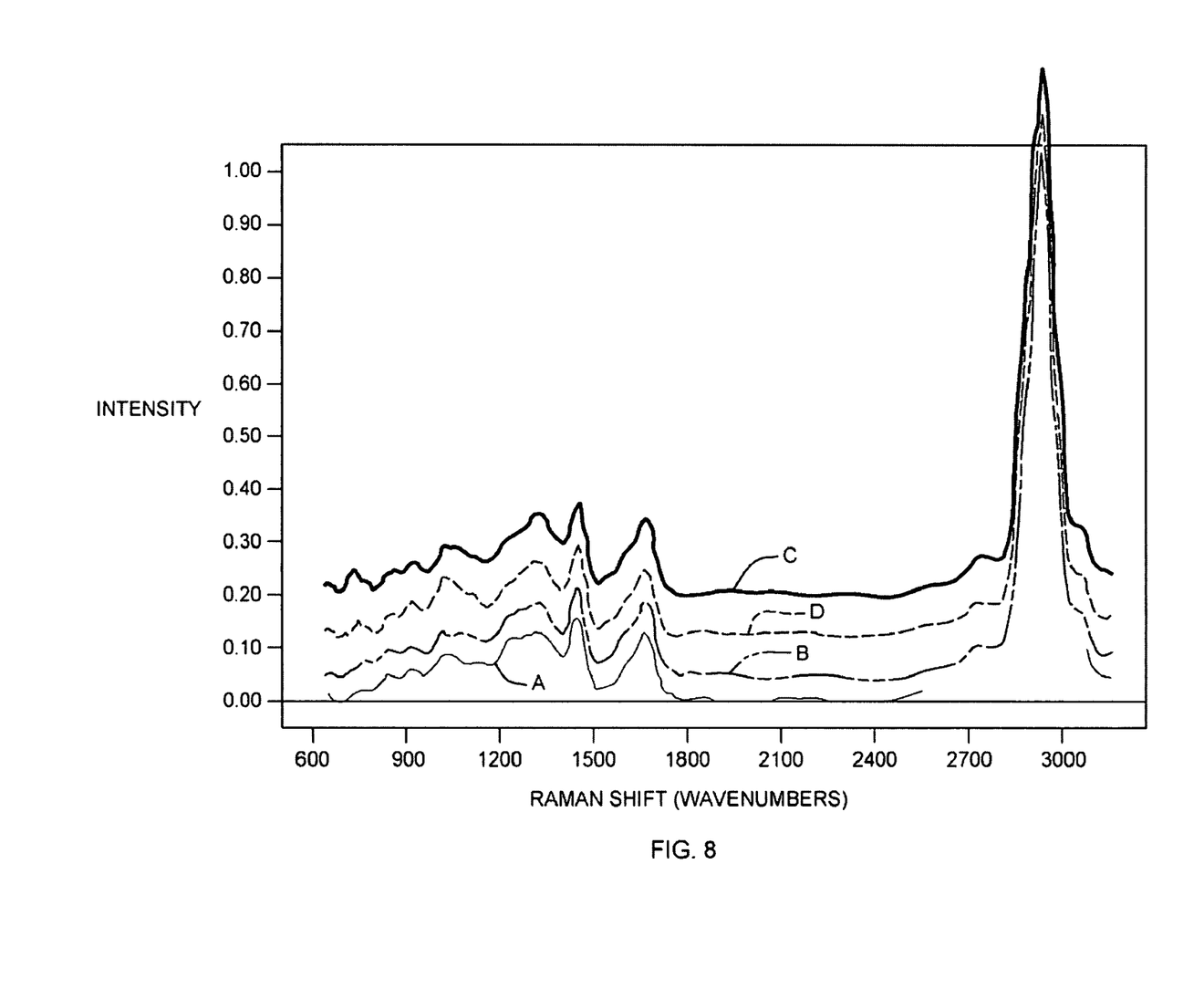
FIG. 8 shows Raman spectra for the corresponding regions of interest illustrated in FIG. 7.
Figure 9:
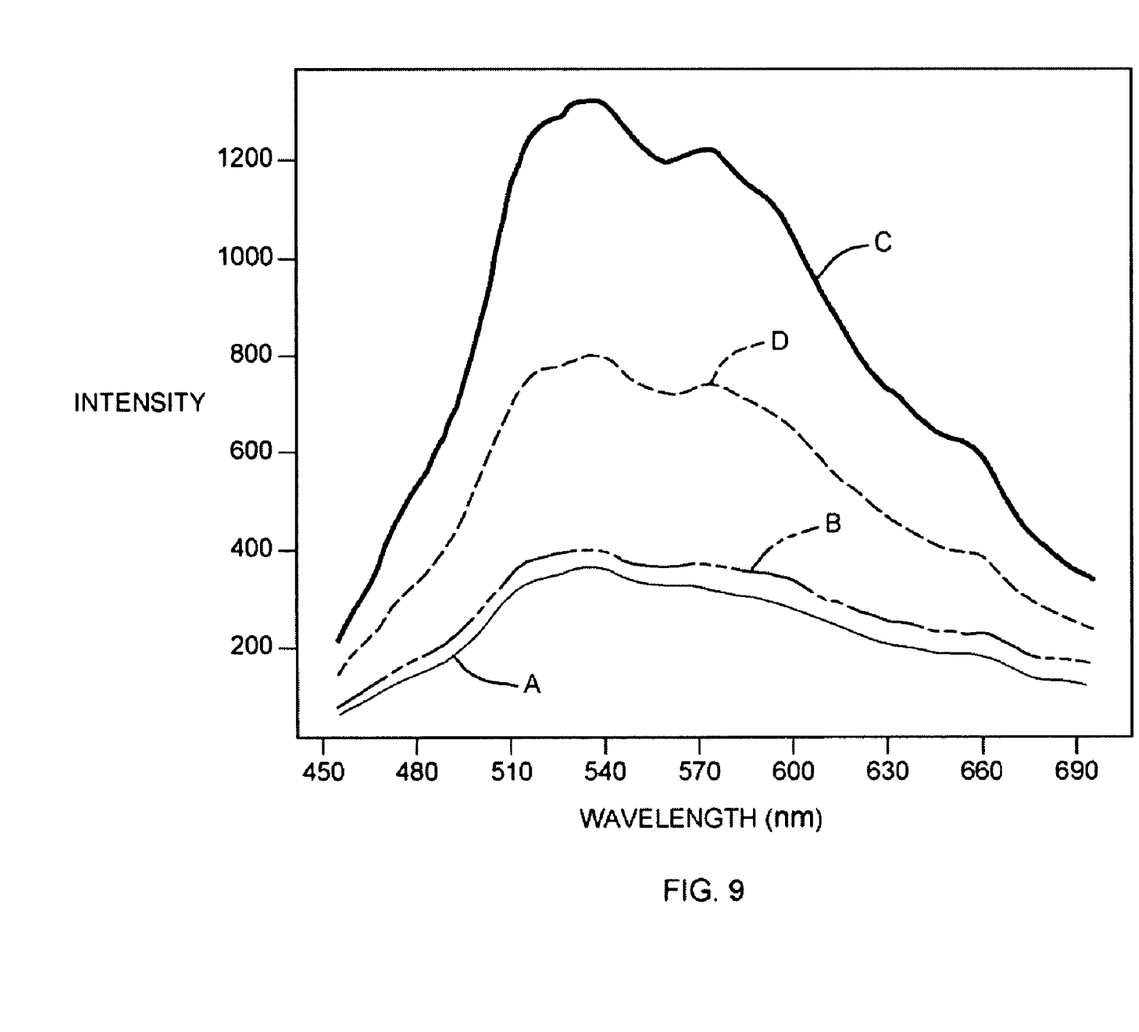
FIG. 9 shows fluorescence spectra for the corresponding regions of interest illustrated in FIG. 7.

Example 1 illustrates a set of image and spectroscopic data for a thin section of kidney tissue mounted on an aluminum coated slide. FIG. 4 shows a digital image for kidney tissue which has not been treated with a contrast enhancing agent. FIGS. 5A-5C show a series of Raman images of the kidney tissue of FIG. 4. FIG. 5A shows a spatially accurate Raman image at 1450 $cm^{-1}$. FIG. 5B shows a spatially accurate Raman image at 1650 $cm^{-1}$. FIG. 5C shows a spatially accurate Raman image at 2930 $cm^{-1}$. FIGS. 6A-B show a series of fluorescence images of the kidney tissue of FIG. 4. FIG. 6A shows a spatially accurate fluorescence image at 515 nm. FIG. 6B shows a spatially accurate fluorescence image at 570 nm. FIG. 7 shows a digital image of the kidney tissue after the tissue was stained with hematoxalin and eosin following standard staining procedures. FIG. 7 shows regions of interest 710, 720, 730 and 740 that are used to extract Raman and fluorescence data sets for searching. FIG. 8 illustrates a subset of Raman spectra for the regions of interest in FIG. 7 where the spectra were extracted from the corresponding regions of interest in the spectroscopic data set: Raman spectrum A corresponds to region of interest 710; Raman spectrum B corresponds to region of interest 720; Raman spectrum C corresponds to region of interest 730; and Raman spectrum D corresponds to region of interest 740. FIG. 9 illustrates fluorescence spectra for the regions of interest in FIG. 7 where the spectra were extracted from the corresponding regions of interest in the spectroscopic data set: fluorescence spectrum A corresponds to region of interest 710; fluorescence spectrum B corresponds to region of interest 720; fluorescence spectrum C corresponds to region of interest 730; and fluorescence spectrum D corresponds to region of interest 740.

Figure 10:
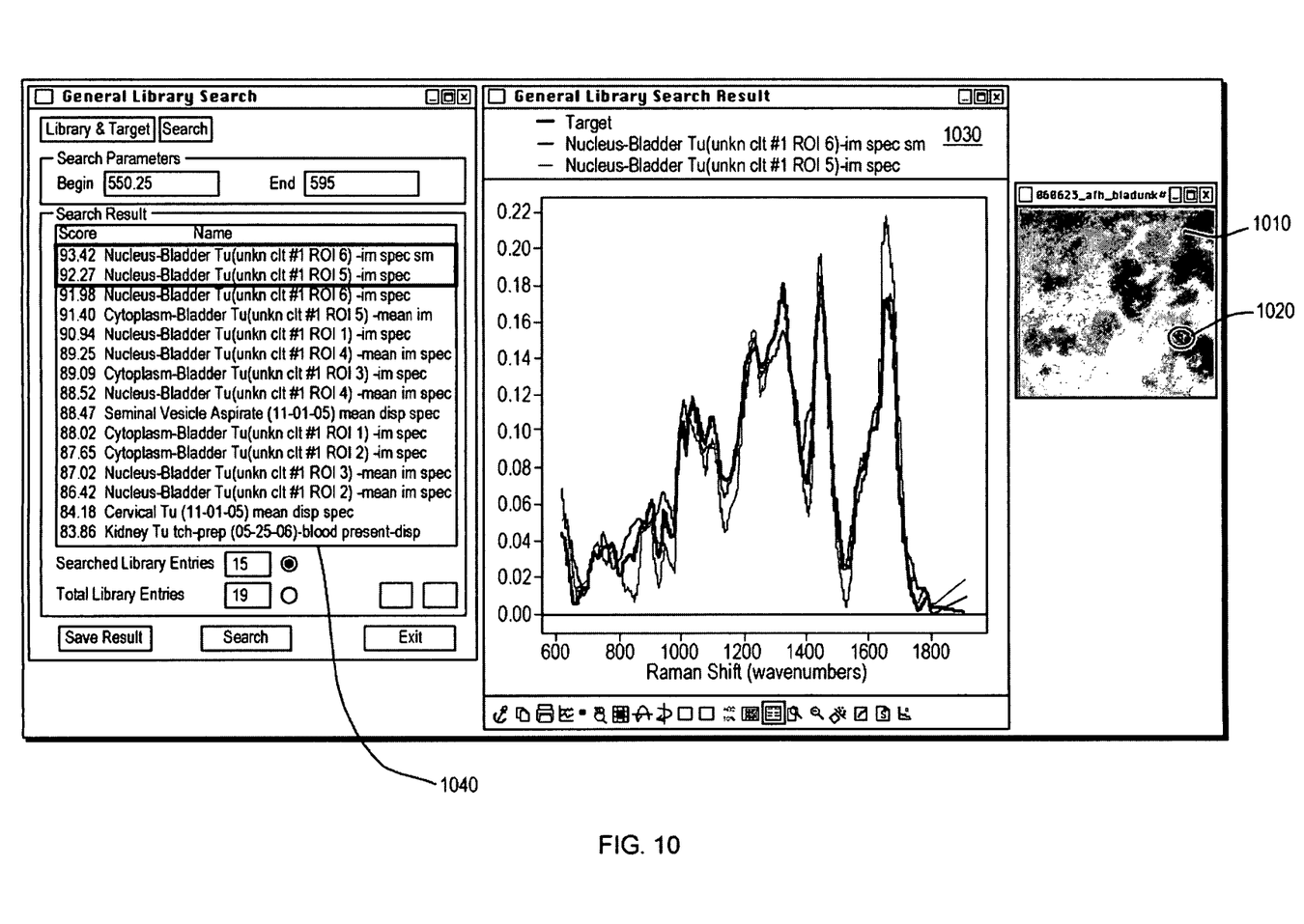
FIG. 10 shows an exemplary graphical user interface used to perform the method of the present disclosure.

FIG. 10 shows a graphical user interface for an embodiment of a system used in performance of a method of the present disclosure. A digital image 1010 is shown for a piece of bladder tissue stained with Hematoxalin and Eosin following standard staining procedures This digital image 1010 is linked to its Raman spectral dataset. The region of interest 1020 highlighted in the digital image is used to select a subset of the spectral data set for searching. The spectra data set is indicated in the spectral portion 1030 of FIG. 10. A subset of the spectral image dataset, in the form of a spectral trace, was searched against a database using Euclidian distance as a metric. The results of the search are evident in the left frame 1040. The correct classification of the region of interest is a nucleus from a bladder tumor. The disease classification of the samples in the database was obtained by pathological characterization. The spectra data search results, in the left frame 1040, identified nucleus from a bladder tumor as the top two ranked results.

The present disclosure may be embodied in other specific forms without departing from the spirit or essential attributes of the disclosure. Accordingly, reference should be made to the appended claims, rather than the foregoing specification, as indicating the scope of the disclosure. Although the foregoing description is directed to the preferred embodiments of the disclosure, it is noted that other variations and modification will be apparent to those skilled in the art, and may be made without departing from the spirit or scope of the disclosure.

What is claimed:

1. A method comprising:
   positioning a sample in a field of view of a spectroscopic device;
   obtaining a first spectroscopic data set for the sample positioned in said field of view;
   storing positional information about said field of view;
   treating the sample with a contrast enhancing agent;
   repositioning the treated sample in said field of view of the spectroscopic device using said stored positional information about said field of view;
   obtaining a digital image of the treated sample positioned in said field of view; and
   linking said first spectroscopic data set with said digital image.

2. The method of claim 1, further comprising:
   providing a database having a plurality of spectroscopic data sets, wherein each spectroscopic data set is linked to a corresponding digital image, and wherein each spectroscopic data set is associated with a known sample and each corresponding digital image is associated with the known sample treated with a contrast enhancing agent; and
   for said first spectroscopic data set, searching said database to thereby identify a second spectroscopic data set therein that matches said first spectroscopic data set.

3. The method of claim 1, wherein said linking comprises:
   defining a transformation to map a plurality of image spatial coordinates for said digital image to a corresponding plurality of spectral spatial coordinates for said first spectroscopic data set;
   identifying one or more image spatial coordinates that define a region of interest in said digital image; and
   identifying a corresponding region of interest in said first spectroscopic data set based on said transformation, wherein said first spectroscopic data set comprises one or more spatially accurate wavelength resolved spectroscopic images.

4. The method of claim 3 further comprising:
   storing one or more of the following: said digital image, said spectroscopic data set, said plurality of image spatial coordinates and said corresponding plurality of spectral spatial coordinates.

5. The method of claim 2, wherein said plurality of spectroscopic data sets includes one or more of the following: a plurality of spectra, and a plurality of spatially accurate wavelength resolved spectroscopic images.

6. The method of claim 5, wherein said plurality of spectra comprises a plurality of Raman spectra and said plurality of spatially accurate wavelength resolved spectroscopic images comprise a plurality of spatially accurate wavelength resolved Raman images.

7. The method of claim 5, wherein said plurality of spectra comprises a plurality of fluorescence spectra and said plurality of spatially accurate wavelength resolved spectroscopic images comprise a plurality of spatially accurate wavelength resolved fluorescence images.

8. The method of claim 2, wherein said sample and said known sample comprise at least one of the following: tissue, tissue microarray, protein microarray, DNA microarray, cell and western blot.

9. The method of claim 1, wherein said first spectroscopic data set comprises one or more of the following: a plurality of Raman spectra of the sample, and a plurality of spatially accurate wavelength resolved Raman images of the sample.

10. The method of claim 1, wherein said first spectroscopic data set comprises one or more of the following: a plurality of fluorescence spectra of the sample, and a plurality of spatially accurate wavelength resolved fluorescence images of the sample.

11. The method of claim 1, wherein said contrast enhancing agent comprises at least one of the following: a stain, a haematoxylin and eosin stain, phosphototungstic acid haematoxylin, silver nitrate, silver metal, gold ions, gold metal, osmium (VIII) oxide and immunohistochemically targeted fluorescent stains.

12. The method of claim 1 further comprising:
    prior to treating the sample, obtaining a second digital image of the sample positioned in said field of view.

13. A storage medium containing machine readable program code, which, when executed by a processor, causes said processor to perform the following:
    obtain a first spectroscopic data set for a sample positioned in a field of view of a spectroscopic device;
    store positional information about said field of view;
    after the sample is treated with a contrast enhancing agent, monitor the repositioning of the treated sample in said field of view of the spectroscopic device using said stored positional information about said field of view;
    obtain a digital image of the treated sample positioned in said field of view;
    store said digital image and said first spectroscopic data set; and
    link said first spectroscopic data set with said digital image.

14. The storage medium of claim 13, wherein said machine readable program code, when executed by said processor, causes said processor to further perform the following:
    for said first spectroscopic data set, search a database having a plurality of spectroscopic data sets to thereby identify a second spectroscopic data set therein that matches said first spectroscopic data set, wherein each spectroscopic data set in said database is linked to a corresponding digital image, and wherein each spectroscopic data set in said database is associated with a known sample and each corresponding digital image is associated with the known sample treated with a contrast enhancing agent.

15. A system comprising:
    means for positioning a sample in a field of view of a spectroscopic device;
    means for obtaining a spectroscopic data set for the sample positioned in said field of view;
    means for storing positional information about said field of view;

means for treating the sample with a contrast enhancing agent;

means for repositioning the treated sample in said field of view of the spectroscopic device using said stored positional information about said field of view;

means for obtaining a digital image of the treated sample positioned in said field of view; and means for linking said spectroscopic data set with said digital image.

16. A system comprising:

a spectroscopic device;

an imaging device;

a machine readable program code containing executable program instructions; and a processor operatively coupled to said spectroscopic device and said imaging device and configured to execute said machine readable program code so as to perform the following:

using said spectroscopic device, obtain a first spectroscopic data set for a sample positioned in a field of view of said spectroscopic device;

store positional information about said field of view;

after the sample is treated with a contrast enhancing agent, monitor the repositioning of the treated sample in said field of view of the spectroscopic device using said stored positional information about said field of view;

using said imaging device, obtain a digital image of the treated sample positioned in said field of view;

store said digital image and said first spectroscopic data set; and link said first spectroscopic data set with said digital image.

17. The system of claim 16, further comprising:

a database having a plurality of spectroscopic data sets, wherein each spectroscopic data set is linked to a corresponding digital image, and wherein each spectroscopic data set is associated with a known sample and each corresponding digital image is associated with the known sample treated with a contrast enhancing agent;

wherein said processor, upon executing said machine readable program code, is configured to further perform the following:

for said first spectroscopic data set, search said database to thereby identify a second spectroscopic data set therein that matches said first spectroscopic data set.

18. The system of claim 16, wherein said processor further configured to facilitate the following:

define a transformation to map a plurality of image spatial coordinates for said digital image to a corresponding plurality of spectral spatial coordinates for said first spectroscopic data set;

identify one or more image spatial coordinates that define a region of interest in said digital image; and identify a corresponding region of interest in said first spectroscopic data set based on said transformation, wherein said first spectroscopic data set comprises one or more spatially accurate wavelength resolved spectroscopic images.

19. The system of claim 17, wherein said plurality of spectroscopic data sets includes one or more of the following: a plurality of spectra, and a plurality of spatially accurate wavelength resolved spectroscopic images.

20. The system of claim 19, wherein said plurality of spectra comprises a plurality of Raman spectra and said plurality of spatially accurate wavelength resolved spectroscopic images comprise a plurality of spatially accurate wavelength resolved Raman images.

21. The system of claim 19, wherein said plurality of spectra comprises a plurality of fluorescence spectra and said plurality of spatially accurate wavelength resolved spectroscopic images comprise a plurality of spatially accurate wavelength resolved fluorescence images.

22. The system of claim 17, wherein said sample and said known sample comprise at least one of the following: tissue, tissue microarray, protein microarray, DNA microarray, cell and western blot.

23. The system of claim 16, wherein said first spectroscopic data set comprises one or more of the following: a plurality of Raman spectra of the sample, and a plurality of spatially accurate wavelength resolved Raman images of the sample.

24. The system of claim 16, wherein said first spectroscopic data set comprises one or more of the following: a plurality of fluorescence spectra of the sample, and a plurality of spatially accurate wavelength resolved fluorescence images of the sample.

25. The system of claim 16, wherein said contrast enhancing agent comprises at least one of the following: a stain, a haematoxylin and eosin stain, phosphototungstic acid haematoxylin, silver nitrate, silver metal, gold ions, gold metal, osmium (VIII) oxide and immunohistochemically targeted fluorescent stains.

26. The system of claim 16, wherein said processor further configured to execute said machine readable program code so as to perform the following:

prior to treating the sample, obtain an second digital image of the sample positioned in said field of view.

* * * * *